(12) United States Patent
Birnbaum et al.

(10) Patent No.: US 10,577,642 B2
(45) Date of Patent: *Mar. 3, 2020

(54) METHOD AND APPARATUS FOR MEASURING PROTEIN POST-TRANSLATIONAL MODIFICATION

(71) Applicant: ICAGEN, INC., Durham, NC (US)

(72) Inventors: Eva R. Birnbaum, Los Alamos, NM (US); Benjamin P. Warner, Los Alamos, NM (US); Sharon M. Baldwin, Santa Fe, NM (US); Jennifer A. Berger, Los Alamos, NM (US); Lori J. Peterson-Court, Los Alamos, LA (US); Michael N. Harris, Los Alamos, NM (US); Rebecca L. E. Miller, Los Alamos, NM (US)

(73) Assignee: Icagen, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/961,480

(22) Filed: Apr. 24, 2018

(65) Prior Publication Data

US 2018/0237823 A1   Aug. 23, 2018

Related U.S. Application Data

(63) Continuation of application No. 15/052,914, filed on Feb. 25, 2016, now Pat. No. 9,976,172, which is a
(Continued)

(51) Int. Cl.
  *C12Q 1/48* (2006.01)
  *C12Q 1/37* (2006.01)
  (Continued)

(52) U.S. Cl.
  CPC .............. *C12Q 1/485* (2013.01); *C12Q 1/37* (2013.01); *G01N 21/75* (2013.01); *G01N 23/223* (2013.01);
  (Continued)

(58) Field of Classification Search
  None
  See application file for complete search history.

(56) References Cited

U.S. PATENT DOCUMENTS

| 4,436,826 A | 3/1984 | Wang |
| 4,663,277 A | 5/1987 | Wang |
| (Continued) | | |

OTHER PUBLICATIONS

Finney et al. "X-ray fluorescence microscopy revelas large-scale relocation and extracellular tranlocation of cellular D copper during angiogenesis" PNAS, vol. 104, No. 7, Feb. 13, 2007, pp. 2247-2252.
(Continued)

*Primary Examiner* — Dirk R Bass
(74) *Attorney, Agent, or Firm* — Morgan, Lewis & Bockius LLP

(57) ABSTRACT

The present invention includes a method for analyzing reactions. The method includes the steps of providing a solution of at least one acceptor chemical and at least one donor chemical. The donor chemical is capable of donating a chemical moiety to the acceptor chemical. The solution further includes at least one controller chemical that affects the reaction between the donor chemical and the acceptor chemical. The solution is then incubated so that a portion of the acceptor chemical reacts with the donor chemical to form an acceptor product. Unreacted donor chemical is separated from the acceptor product. The acceptor product or the donor chemical is then measured using X-ray fluorescence. Another aspect of the present invention includes a method for analyzing protein function. The method includes the steps of providing a solution of at least one acceptor chemical and at least one donor chemical. The donor chemical is capable of donating a chemical moiety to the acceptor chemical. The donor chemical includes a functional group selected from ester, anhydride, imide, acyl halide, and amide. The solution is then incubated so that a portion of the
(Continued)

acceptor chemical reacts with the donor chemical to form an acceptor product. Unreacted donor chemical is separated from the acceptor product. The acceptor product or the donor chemical is then measured using X-ray fluorescence. Yet another aspect of the present invention includes a method for analyzing protein function. The method includes the steps of providing a solution of at least one acceptor chemical and at least one donor chemical. The solution is then incubated so that a portion of the acceptor chemical reacts with the donor chemical to form an acceptor product. Unreacted donor chemical is separated from the acceptor product. The acceptor product or the donor chemical is then measured using X-ray fluorescence. An additional analytical method is also used to measure either the acceptor product or the donor chemical.

13 Claims, 3 Drawing Sheets

Related U.S. Application Data continuation of application No. 12/239,459, filed on Sep. 26, 2008, now abandoned.

(60) Provisional application No. 60/995,997, filed on Sep. 28, 2007.

(51) Int. Cl.
  *G01N 21/75* (2006.01)
  *G01N 33/20* (2019.01)
  *G01N 23/223* (2006.01)
  *G01N 33/68* (2006.01)

(52) U.S. Cl.
  CPC ......... *G01N 33/20* (2013.01); *G01N 33/6842* (2013.01); *G01N 2223/076* (2013.01); *G01N 2333/91215* (2013.01); *G01N 2333/96441* (2013.01); *Y10T 436/17* (2015.01); *Y10T 436/200833* (2015.01)

(56) References Cited

U.S. PATENT DOCUMENTS

| | | |
|---|---|---|
| 5,216,126 A | 6/1993 | Cox |
| 5,902,723 A | 5/1999 | Dower |
| 6,329,209 B1 | 12/2001 | Wagner |
| 6,344,334 B1 | 2/2002 | Ellman |
| 6,391,590 B1 | 5/2002 | Sano |
| 6,858,148 B2 | 2/2005 | Warner |
| 7,519,145 B2 | 4/2009 | Warner |
| 7,858,385 B2 | 12/2010 | Warner |
| 8,238,515 B2 | 8/2012 | Birnbaum |
| 8,431,357 B2 | 4/2013 | Birnbaum |
| 2003/0027129 A1 | 2/2003 | Warner et al. |
| 2003/0215804 A1 | 11/2003 | Berggren et al. |
| 2004/0235059 A1 | 11/2004 | Warner |
| 2008/0220441 A1 | 9/2008 | Birnbaum |

OTHER PUBLICATIONS

Ruiz et al. "Quantification of Pt bound to DNA using total-reflection X-ray fluorescence (TXRF)" Analyst, 1999, 124, 583-585.

Martin et al. "Quantitative analysis of protein phophorylation status and protein kinase activity on microarrays using a novel fluorescent phophorylation sensor dye" Proteomics, 2003, 3, pp. 1244-1255.

Jagade et al. "Role of protein kinases in signal transduction and their inhibitors", Pharmacologyonline 2: 371-384 (2010).

Piotrowska et al. "Biological activity of piceatannol: Leaving the shadow of resveratrol", Mutation Research 750 (2013) 60-82.

Shimazaki et al. "Involvement of Calmodulin and Calmodulin-Dependent Myosin Light Chain Kinase in Blue Light-Dependent H+ Pumping by Guard Cell Protoplasts from *Vicia faba* L.", Plant Physiol. (1992) 99, 1416-1421.

Tation et al. "The Src-selective Kinase Inhibitor PP1 Also Inhibits Kit and Bcr-Abl Tyrosine Kinases", The Journal o Biological Chemistry, vol. 278, Issue of Feb. 14, pp. 4847-4853, 2004.

Tation et al. "The Src-selective Kinase Inhibitor PP1 Also Inhibits Kit and Bcr-Abl Tyrosine Kinases", The Journal of Biological Chemistry, vol. 278, Issue of Feb. 14, pp. 4847-4853, 2004.

Moll et al., "Ionic Inhibition of Catalytic Phosphorylation of Histone by Bovine Braine Protein Kinase", May 1977, Journal of Biological Chemistry, issue 252, pp. 3007-3011.

METHOD AND APPARATUS FOR MEASURING PROTEIN POST-TRANSLATIONAL MODIFICATION

RELATED APPLICATIONS

This application is a continuation application of U.S. application Ser. No. 15/052,914 (now U.S. Pat. No. 9,976,172), filed on Feb. 25, 2016, which is a continuation application of U.S. application Ser. No. 12/239,459, filed on Sep. 26, 2008, which claims the priority of U.S. Provisional Patent Application 60/995,997 entitled "Method and Apparatus for Measuring Protein Post-Translational Modification," which was filed on Sep. 28, 2007, the entireties of which are incorporated by reference herein.

FIELD OF THE INVENTION

The present invention relates to the analysis of protein function.

BACKGROUND OF THE INVENTION

Post-translational modifications are chemical changes to proteins that occur after the primary structure of the protein has been completed via translation. Post-translational modifications include, but are not limited to, phosphorylation, dephosphorylation, proteolysis, protein ligation, glycosylation, sulfation, methylation, and ubiquitination.

Post-translational modifications influence protein behavior. For example, insulin is formed by the post-translational modification of proinsulin, which itself is formed by the post-translational modification of preproinsulin. The post-translational addition or removal of phosphorus from proteins plays a regulatory role in many biochemical pathways and signal transduction pathways.

The analysis of post-translational modifications often requires labor intensive sample preparation and expensive or hazardous chemical reagents such as radioactive materials. For example, protein kinase assays often include the use of radioactively labeled ATP as phosphate donor to a substrate peptide or protein. Following the kinase reaction, the substrate is separated from unreacted radioactive ATP. Any radioactivity incorporated into the substrate is measured, such as by scintillation counting. This assay has drawbacks. The assay generates radioactive waste. Radioactive phosphorus has a short half life, so fresh reagent must be frequently acquired. The assay requires at least micromolar concentrations of ATP, which is one thousand times greater than the millimolar biological concentration of ATP. The concentration of substrate in the assay is often much higher than expected substrate concentrations in vivo.

There remains a need for simpler methods for measuring post-translational modification. The present invention is designed to address that need.

SUMMARY OF THE PRESENT INVENTION

One aspect of the present invention includes a method for analyzing reactions. The method includes the steps of providing a solution of at least one acceptor chemical and at least one donor chemical. The donor chemical is capable of donating a chemical moiety to the acceptor chemical. The solution further includes at least one controller chemical that affects the reaction between the donor chemical and the acceptor chemical. The solution is then incubated so that a portion of the acceptor chemical reacts with the donor chemical to form an acceptor product. Unreacted donor chemical is separated from the acceptor product. The acceptor product or the donor chemical is then measured using X-ray fluorescence.

Another aspect of the present invention includes a method for analyzing protein function. The method includes the steps of providing a solution of at least one acceptor chemical and at least one donor chemical. The donor chemical is capable of donating a chemical moiety to the acceptor chemical. The donor chemical includes a functional group selected from ester, anhydride, imide, acyl halide, and amide. The solution is then incubated so that a portion of the acceptor chemical reacts with the donor chemical to form an acceptor product. Unreacted donor chemical is separated from the acceptor product. The acceptor product or the donor chemical is then measured using X-ray fluorescence.

Yet another aspect of the present invention includes a method for analyzing protein function. The method includes the steps of providing a solution of at least one acceptor chemical and at least one donor chemical. The solution is then incubated so that a portion of the acceptor chemical reacts with the donor chemical to form an acceptor product. Unreacted donor chemical is separated from the acceptor product. The acceptor product or the donor chemical is then measured using X-ray fluorescence. An additional analytical method is also used to measure either the acceptor product or the donor chemical.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

FIGURES

DETAILED DESCRIPTION

Figure 1:
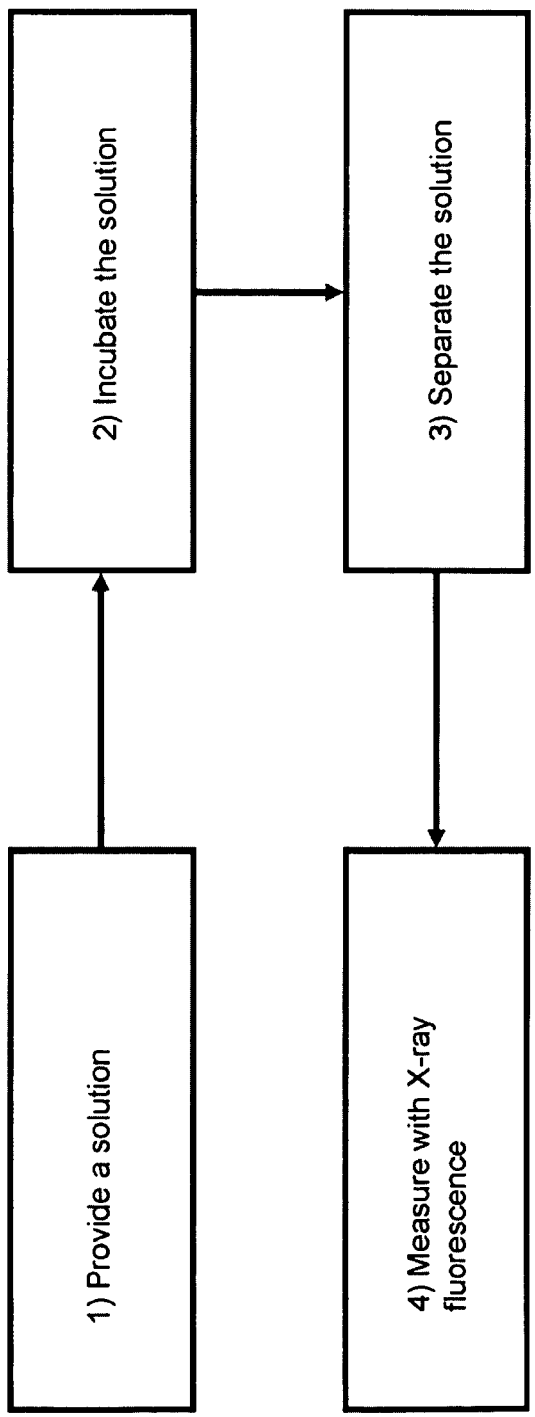
FIG. 1 shows a flowchart depicting the steps in the method of the present invention.

An embodiment of the present invention is a method to determine the effect of chemicals on proteins and protein function, as depicted in the flowchart in FIG. 1. The invention comprises the steps of providing a solution (FIG. 1, Box 1), incubating the solution, and measuring the solution. The solution comprises a solvent, an acceptor chemical, a donor chemical, and a controller chemical. The solution is incubated for a period of time sufficient for a portion of the donor chemical to react with a portion the acceptor chemical to form a donor product and an acceptor product (FIG. 1, Box 2). The donated chemical element can be donated alone or as part of a chemical moiety or functional group. Any unreacted donor chemical is then separated from the acceptor product (FIG. 1, Box 3). Either the unreacted donor chemical or the acceptor product is then measured using X-ray fluorescence (FIG. 1, Box 4).

A second embodiment of the present invention is a method to determine the activity of proteins. The second embodiment comprises the steps of providing a solution comprising at least one acceptor chemical and at least one donor chemical (FIG. 1, Box 1). The donor chemical is capable of donating a chemical element to the acceptor chemical to form an acceptor product. The donated chemical element can be donated alone or as part of a chemical moiety or functional group. In the second embodiment, the donor comprises a functional group selected from ester, anhydride, amide, and combinations thereof. The solution is then incubated to allow at least a portion of the acceptor chemical to react with the donor chemical to form a product chemical (FIG. 1, Box 2). The donor chemical and the acceptor product are then separated (FIG. 1, Box 3). The donor chemical or the acceptor product is then measured using X-ray fluorescence (FIG. 1, Box 4). The solution of the second embodiment of the present invention preferably also comprises at least one controller chemical.

Figure 2:
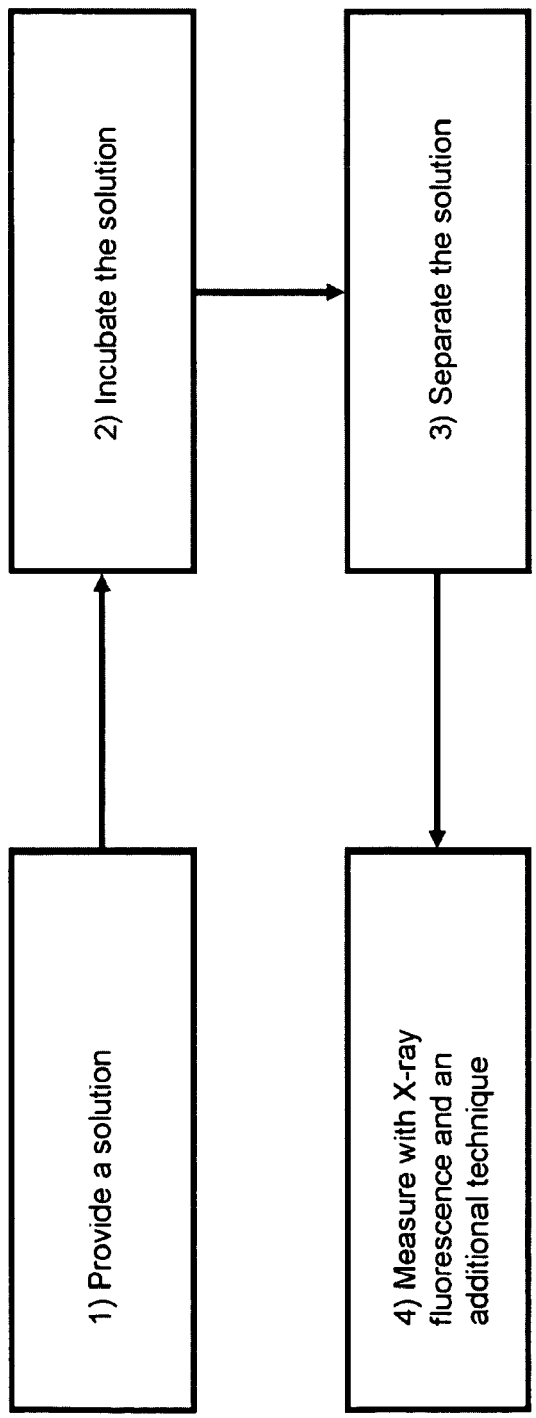
FIG. 2 shows a flowchart depicting the steps in another method of the present invention.

A third embodiment of the present invention is a method to determine the activity of proteins, as depicted in FIG. 2. The third embodiment comprises the steps of providing a solution comprising at least one acceptor chemical and at least one donor chemical (FIG. 2, Box 1). The donor chemical is capable of donating a chemical element to the acceptor chemical to form an acceptor product. The donated chemical element can be donated alone or as part of a chemical moiety or functional group. The solution is incubated to allow a portion of the acceptor chemical to react with the donor chemical to form a product chemical (FIG. 2, Box 2). Unreacted donor chemical is then separated from the acceptor product (FIG. 2, Box 3). The donor chemical or the acceptor product is then measured using X-ray fluorescence (FIG. 2, Box 4). The chemical that is measured using X-ray fluorescence is also quantified using a second measurement technique (FIG. 2, Box 4).

The solution comprises a solvent, an acceptor chemical, and a donor chemical. The solvent preferably does not contain at least one of the elements selected from the list phosphorus, sulfur and chlorine. The solvent is more preferably water, and most preferably the solvent is buffered water.

The solution is allowed to incubate for a reaction to occur. In the present invention, incubate refers to allowing the reaction to proceed at any temperature.

Many chemicals require a buffer to maintain the pH within a particular range (e.g. a pH buffer), or to maintain the redox state of a chemical (e.g. a redox buffer), or to maintain an ionic strength (e.g. an isotonic buffer). Many buffers contain elements which might interfere with the measurement of the chemical. The buffer should preferably be free of at least one chemical element having an atomic number of greater than four, where that chemical element is present in the donor chemical or acceptor molecule. The buffer should more preferably be free of at least one chemical element having an atomic number of greater than eight, where that chemical element is present in the donor chemical or acceptor product. The buffer should preferably be free of at least one of the following chemicals or functional groups: dimethylsulfoxide, thiols, sulfate anion, sulfonate anions, chloride anion, bromide anion, fluoride anion, iodide anion, perchlorate anion, phosphate anion, and phosphonate anions. The buffer preferably comprises one or more of the following chemical or functional groups: amine, imine, nitrate anion, nitrite anion, ammonium cation, acetate anion, carboxylate anion, conjugate bases of carboxylic acids, carbonate anion, and iminium cation; these chemicals offer the correct buffering properties with minimal X-ray fluorescence interference.

The solution may be redox buffered using chemicals such as dithiothreitol (DTT) or tris(2-carboxyethyl)phosphine (TCEP). However, it is highly preferable that the substrate is separated from any phosphorus or sulfur in the redox buffer. Preferred redox buffers do not contain phosphorus or sulfur, or else they are solid supported such as Immobilized TCEP Disulfide Reducing Gel, which is available from Thermo Fisher Scientific Inc. PO Box 117, Rockford, Ill. 61105 USA.

The donor chemical comprises an element having an atomic number of greater than eight. The donor chemical reacts with the acceptor chemical to transfer this chemical element having an atomic number greater than eight, either by itself or as part of a larger chemical group, to the acceptor chemical to form an acceptor product. The element to be donated is preferably selected from the list sulfur, phosphorus, selenium, chlorine, bromine, iodine, functional groups comprising at least one of these chemical elements, and combinations thereof. After the donor chemical has reacted to transfer the chemical element having an atomic number greater than eight, the donor chemical is called the donor product. The donor chemical preferably comprises at least one of the chemical functional groups selected from the list of anhydride, ester, amide, imide, acyl halides, and combinations thereof. Functional groups include those not based on carbon, such as anhydrides or phosphoric acid, phosphonic acid, their sulfur analogs, and the like are considered to be anhydrides; esters such as phosphoric esters and phosphonic esters and their sulfur analogs are considered to be esters; amides such as phosphoric amides and phosphonic amides and their sulfur analogs and the like are considered to be amides; imides such as phosphoric imides and phosphonic imides and their sulfur analogs and the like are considered to be imides; acyl halides such as phosphoryl halides and phosphonyl halides and their sulfur analogs and the like are considered to be acyl halides. Examples of donor chemicals are adenosine triphosphate, inosine triphosphate, guanosine-5'-triphosphate, and 3'-phosphoadenosine-5'-phosphosulfate. The donor chemical preferably has a concentration of less than about 100 millimolar.

The acceptor chemical reacts with the donor chemical to accept a chemical element having a chemical element having an atomic number greater than eight, either by itself or as part of a larger chemical group, from the donor chemical. The acceptor chemical preferably also comprises at least one element having an atomic number greater than eight that is not the same as the element donated by the donor chemical; if this is the case, then the efficiency of the reaction between the donor chemical and the acceptor chemical may be calculated from the measured values of these two elements. For example, if the acceptor chemical comprises a sulfur atom, and the donated functional group comprises a phosphorus atom, then the ratio of the phosphorus X-ray fluorescence signal to the sulfur X-ray fluorescence signal allows the completeness of the reaction to be measured with a single measurement technique. The acceptor chemical preferably contains at least one of the functional groups R—$NH_2$, RN(X)H, R—O—H, R—$O^-$, R—S—H, R—$S^-$ where R is carbon or hydrogen, and X may be any chemical element, R—$O^-$ refers to an alkoxide anion or aryloxide anion, and R—$S^-$ refers to an alkyl or aryl thiolate anion. Examples of acceptor chemicals are proteins, amino acids, peptides, polymers comprising amino acids, oligomers comprising amino acids, nucleotides, polymers comprising nucleotides, oligomers comprising nucleotides, and water. The acceptor chemical preferably has a concentration of less than about 100 millimolar.

The reaction between the donor chemical and the acceptor chemical preferably forms or breaks at least one covalent bond.

The solution comprises one or more controller chemicals. The controller chemicals may accelerate the rate of the reaction between the donor chemical and the acceptor chemical. The controller chemicals may decelerate the rate of the reaction between the donor chemical and the acceptor chemical. The controller chemicals may increase or decrease the turnover number of a catalyst. Different controller chemicals in the same solution may accelerate or decelerate the reaction between the acceptor chemical and the donor chemical by various amounts. Examples of controller chemicals are adenosine diphosphate; phthalene-1-sulfonyl)-1H-hexahydro-1,4-diazepine; 1-(5-Isoquinolinesulfonyl)-1H-hexahydro-1,4-diazepine; 1-(5-Isoquinolinesulfonyl)-2-methylpiperazine; 1-(5-Isoquinolinesulfonyl)-piperazine; 1,2-Dimethoxy-N-methyl(1,3)benzodioxolo(5,6-c) phenanthridinium chloride; 1-[N,O-bis-(5-Isoquinolinesulfonyl)-N-methyl-L-tyrosyl]-4-phenyl-piperazine; 2-(4-Morpholinyl)-8-phenyl-4H-1-benzopyran-4-one; 2,3-Dihydro-N,N-dimethyl-2-oxo-3-[(4,5,6,7-tetrahydro-1H-indol-2-yl)methylene]-1H-indole-5-sulfonamide; 2,5-Dihydroxymethylcinnamate; 2-Cyano-N-(2,5-dibromophenyl)-3-hydroxy-2-butenamide; 3-[[4-(dimethylamino)phenyl]methylene]-1,3-dihydro-2H-indol-2-one; Dihydroxy-benzylamino)benzoic Acid Adamantan-1-yl Ester; 4-(3-chloro-4-fluoroanilino)-7-methoxy-6-(3-morpholino propoxy) quinazoline; 4,5,6,7-Tetrabromo-2-azabenzimidazole; 4-[(3-Bromophenyl)amino]-6,7-dimethoxyquinazoline; 4-amino-5-(4-chlorophenyl)-7-(t-butyl)pyrazolo[3,4,d]pyrimidine; 4-Amino-5-(4-methylphenyl)-7-(t-butyl)pyrazolo[3,4-d]pyrimidine; 4-Amino-5-iodo-7-(beta-D-ribofuranosyl) pyrrolo[2,3-d]-pyrimidine; 4'-Amino-6-Hydroxyflavone; 4-Amino-N-(2,5-dihydroxybenzyl)adamantyl Benzoate,; 4-Amino-N-(2,5-dihydroxybenzyl)methyl benzoate; 5,6-Dichloro-1-b-D-ribofuranosyl benzimidazole; 5,7-Dimethoxy-3-(4-pyridinyl)quinoline; 6-Amino-4-methyl-(β-D-ribofuranosyl)4H,8H-pyrrolo[4,3,2-de]pyrimido[4,5-c]pyridazine; Bisindolylmaleimide IX; N-(2'-Guanidinoethyl)-5-isoquinolinesulfonamide; N-(6-Aminohexyl)-5-chloro-1-naphthalenesulfonamide; N-[2-(Methylamino) ethyl]-5-isoquinolinesulfonamide; N-[2-(p-Bromocinnamylamino)ethyl]-5-isoquinolinesulfonamide; N-Benzyl-3,4-dihydroxy-benzylidenecyanoacetamide; Picropodophyllin; Quercetin; rac-2-methyl-1-octadecyl-glycero-(3)-phosphocholine; Rapamycin; Rottlerin; Staurosporine; trans-3,3',4,5'-Tetrahydroxystilbene, 4-[(1E)-2-(3,5-Dihydroxyphenyl)ethenyl]-1,2-benzenediol; trans-4-[(1R)-1-Aminoethyl]-N-4-pyridinylcyclohexanecarboxamide; wortmannin; metal; enzyme inhibitors; protein inhibitors; catalysts; enzymes; proteins; amino acids; peptides; polymers comprising peptides, carbohydrates; lipids; nucleotides; polymers comprising nucleotides; reactive oxygen species; and reactive nitrogen species. The solution preferably includes at least two controller chemicals. The solution preferably comprises at least one controller chemical that increases the rate of reaction between the donor chemical and the acceptor chemical and at least one controller chemical that decreases the rate of reaction between the donor chemical and the acceptor chemical. The solution most preferably includes at least one enzyme; more preferably the solution includes a metal that enhances the activity of this enzyme; and most preferably the solution also includes at least one chemical that inhibits the activity of this enzyme.

The donor chemical, acceptor chemical, controller chemical, or combinations thereof may be chemically attached to a surface or otherwise immobilized.

The donor chemical, acceptor chemical, solvent, or controller chemicals may be derived from biological specimens such as cell cultures, tissue samples, tissue cultures, biopsy samples, blood samples, and the like.

After the solution is allowed to incubate for a period of time sufficient for a portion of the donor chemical to react with a portion of the acceptor chemical, the donor chemical is then separated from the acceptor chemical and acceptor product. The entire solution may be subjected to this separation. Alternatively, a portion of the solution may be subjected to this separation. If a portion of the solution is subjected to a separation, then a kinetic analysis of the reaction may be performed by comparing the amount of the reaction between the donor chemical and the acceptor chemical which has occurred at various times. Other ways to perform kinetic analyses include varying the concentrations of the donor chemical, the acceptor chemical, and any controller chemicals. These concentrations may be varied together or independently.

The separation may be conveniently performed using chromatography, such as gel filtration chromatography or size exclusion chromatography, such as a Quick Spin Protein Column using Sephadex G-25, available from Roche Applied Science, PO Box 50414, Indianapolis, Ind., 46250. This separation is amenable to multiplexing using a well plate format, such as a 96-well, 384-well, or 1536-well plate format. Separations systems such as Zeba 96-well plates available from Pierce Biotechnology Inc., PO Box 117, Rockford, Ill., 61105, are particularly convenient. Separation may be expedited using a centrifuge, such as a the IEC CL40 available from Thermo Fisher Scientific, product # 11210923, 450 Fortune Blvd, Milford, Mass., 01757; or a vacuum manifold, such as a Vacuum apparatus such as the MultiScreen Vacuum manifold with Direct Stack from Millipore, 290 Concord Road, Billerica, Mass. 01821, attached to a standard vacuum pump (for example, Millipore, Catalog # WP61 115 60) also available from Millipore. An alternative method of separation is ultrafiltration, such as might be performed using a Centricon YM-3 centrifuged for 3 hours at 7000 g. Other alternatives include extraction, selective precipitation, and immunoprecipitation. The key characteristic of the separation is that acceptor product and unreacted donor chemical are separated. Separation using a centrifuge is especially convenient, because it allows the use of well plates.

To facilitate the separation, the donor chemical and the acceptor product preferably differ in their molecular weights by a factor of at least 10, and more preferably by a factor of at least 20. This difference in molecular weights will allow convenient separation by ultrafiltration and gel filtration chromatography. Alternatively, the donor chemical and the acceptor product may preferably have different ionic charges at the same pH value. This difference in ionic state allows convenient separation using anion exchange chromatography. Alternatively, the donor chemical and the acceptor product have water-octanol partitioning coefficients that differ by a factor of at least 10, and more preferably by a factor of at least 100. This difference in water-octanol partitioning coefficients allows convenient separation by extraction or many chromatographic methods. The separation preferably separates the donor chemical from the acceptor chemical and the acceptor product.

After the donor chemical and the acceptor product are separated, either or both the donor chemical and the acceptor product are measured using x-ray fluorescence. The measurement may be conveniently obtained using an X-ray fluorescence spectrometer. An XRF spectrometer is an apparatus capable of irradiating a sample with an X-ray beam, detecting the X-ray fluorescence from the sample, and using the X-ray fluorescence to determine which elements are present in the sample and measuring the quantity of these elements. The X-ray fluorescence measurement may be obtained using the EDAX Eagle XPL energy dispersive X-ray fluorescence spectrometer, equipped with a microfocus X-ray tube, lithium drifted silicon solid-state detector, processing electronics, and vendor supplied operating software, available from the EDAX division of Ametek, 91 McKee Drive Mahwah, N.J. 07430. The X-ray fluorescence measurement may be obtained using the ZSX Primus, available from Rigaku Americas, 9009 New Trails Drive, The Woodlands, Tex. 77381. The x-ray fluorescence instrument preferably comprises at least one of the following: a monocapillary focusing optic, polycapillary focusing optic, a collimator, a microfocus X-ray tube, a synchrotron X-ray source, a linear accelerator X-ray source, a rhodium X-ray tube, a molybdenum X-ray tube, a chromium X-ray tube, a silver X-ray tube, a palladium X-ray tube, a monochromatic X-ray source, a polychromatic X-ray source, a polarized X-ray source, a confocal X-ray fluorescence spectrometer focusing arrangement, a PIN diode detector, a semiconductor X-ray detector, a germanium or doped germanium X-ray detector, a silicon or doped silicon X-ray detector, a wavelength dispersive X-ray fluorescence spectrometer, an energy dispersive X-ray fluorescence spectrometer, total reflectance X-ray fluorescence spectrometer, and the like. Preferably, the x-ray excitation source emits x-ray having a polychromatic x-ray excitation spectrum, and more preferably the x-ray excitation source emits x-rays having a spectrum with at least two maxima. Excitation with polychromatic x-rays increases the efficiency for exciting more than one chemical element in the sample being analyzed, or for exciting more than one spectral feature in the chemical analyte being analyzed.

The sample of donor chemical or acceptor product being measured preferably has at least a portion of the solvent removed. Preferably at least 80% of the solvent is removed; more preferably substantially all of the solvent is removed. Evaporation is a convenient method for removing the solvent. The solvent is preferably evaporated using elevated temperatures that are above about 22° C. or reduced atmospheric pressure that is below about 760 torr. The solvent may be conveniently removed using a vacuum centrifuge, such as a Savant Speed Vac Plus SC 250DDA or a Thermo Savant SPD 1010 SpeedVac®.

The sample of donor chemical or acceptor product is preferably concentrated into an area which is comparable in size to the x-ray excitation beam. The area containing more than about 50% of the mass of the sample to be measured should have an area which is within a factor of 100 of the area containing more than about 50% of the x-rays in the x-ray excitation beam. Preferably, the area containing more than about 50% of the sample has an area of less than about 0.005 square centimeters. If the area of x-ray excitation beam as it illuminates the sample is significantly greater than the area of the sample, then x-ray photons are wasted. If the area of x-ray excitation beam as it illuminates the sample is significantly smaller than the area of the sample, then the measurement time will be unnecessarily long or else a portion of the sample will be wasted by its not being measured.

If the solvent containing the sample is evaporated, the dried or partially dried sample of acceptor product or donor chemical is preferably deposited onto a deposition substrate. The deposition substrate is preferably substantially free of at least one of the elements sulfur, phosphorus, or chlorine. Examples of suitable materials for the deposition substrate include Porvair #229302, Porvair #229112, Porvair #229058, Porvair #229304, and Porvair #229301, all of which are available from Porvair plc, Brampton House, 50 Bergen Way, King's Lynn, Norfolk PE30 2JG, U.K.), aluminum foils (examples: Microseal 'F' Foil from Bio-Rad Laboratories, 1000 Alfred Nobel Drive, Hercules, Calif. 94547). Other materials that may be used for the deposition substrate include: Super-Thin Polyester Surface-Protection Tape, Chemical-Resistant Surlyn Surface-Protection Tape, Abrasion-Resistant Polyurethane Surface-Protection Tape, Heat-Resistant Kapton Tape with Silicone Adhesive or with Acrylic Adhesive, UV-Resistant Polyethylene Surface-Protection Tape, Clean-Release Polyethylene Surface-Protection Tape, Low-Static Polyimide Tape, all available from McMaster-Carr, 6100 Fulton Industrial Blvd., Atlanta, Ga. 30336-2852. Other materials which may be used for the deposition substrate include polypropylene, available from Lebow Company, 5960 Mandarin Ave., Goleta, Calif. 93117 U.S.A. Other substrates that are conveniently used for the deposition substrate include AP1, AP3, ProLINE Series 10, ProLINE Series 20, DuraBeryllium substrates from Moxtek, 452 West 1260 North, Orem, Utah 84057. Other materials which may be used for the deposition substrate include Ultralene®, mylar, polycarbonate, prolene, and kapton, available from SPEX CertiPrep Ltd, 2 Dalston Gardens, Stanmore, Middlesex HA7 1BQ, ENGLAND. Other materials that may be used as the deposition substrate include Hostaphan®, polyester, and Etnom® available from Chemplex Industries, Inc., 2820 SW 42nd Avenue, Palm City, Fla. 34990-5573 USA. Another material that may be conveniently used is Zone Free Film Part ZAF-PE-50, available from Excel Scientific, 18350 George Blvd, Victorville, Calif., 92394. Other useful substrates are glass and silicon. This list is not exhaustive, and other materials may be used as the deposition substrate. The deposition substrate is also preferably substantially free of elements which have X-ray fluorescence emission peaks having energies of between 1.9 KeV and 3 KeV, because these peaks tend to interfere with the signals of most interest to biochemical and biological applications. Elements which have X-Ray Fluorescence emission peaks having energies of between 1.9 KeV and 3 KeV are: osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. If an x-ray fluorescence spectrometer is used which uses an x-ray detector which comprises silicon, then the deposition substrate is also preferably free of elements which have X-Ray Fluorescence escape peaks (i.e. x-ray fluorescence emission peaks minus 1.74 KeV) having energies of between 1.9 KeV and 3 KeV, because these escape peaks tend to interfere with the signals of most interest for biochemical and biological applications. Elements which have X-Ray Fluorescence escape peaks having energies of between 1.9 KeV and 3 KeV are: calcium, tellurium, iodine, scandium, xenon, cesium, barium, titanium, and lanthanum. "Substantially free" is defined herein as being less than about 4% by weight. The deposition substrate may have additional chemical elements, which may be used for measuring the thickness of the sample. If wavelength dispersive x-ray fluorescence is used, then the elemental purity of the deposition substrate is not as important; in this case, the film should be substantially free of the element or elements which are being used to quantify the sample. The deposition substrate may be treated to increase protein adhesion; a non-inclusive list of treatments includes treating the deposition substrate with oxygen or nitrogen plasma or with poly-lysine.

The chemical measured using x-ray fluorescence may be measured using one or more second analytical techniques. Examples of second analytical techniques include the addition of standard or internal standard that may be measured using x-ray fluorescence; other spectrometric techniques than x-ray fluorescence such as radiometric analysis or added radioactive materials, ultraviolet or visible spectrometry, infrared spectrometry, surface plasmon resonance, nuclear magnetic resonance spectrometry, terahertz spectrometry, microwave spectrometry, surface plasmon resonance spectrometry, mass spectrometry. An example of a second analytical technique is the Quick Start Bradford Protein Assay, available from Bio-Rad Laboratories, Inc., 2000 Alfred Nobel Dr., Hercules, Calif. 94547 USA, and performed according to manufacturer's instructions. Any of these techniques may be used with or without added standards, dyes, tracers, and the like.

EXAMPLES

Example 1. NAD+ kinase served as the acceptor chemical and as a controller chemical. Adenosine triphosphate served as the donor chemical. Magnesium chloride and acetic acid served as controller chemicals. Phosphorylated NAD kinase served as the acceptor product. Adenosine diphosphate served as the donor product. A solution was prepared by combining 100 microliters of a solution of NAD kinase [880 micromolar] in water with a 200 microliters of a solution of adenosine triphosphate [5 millimolar], magnesium chloride [10 millimolar], tris(hydroxymethyl)aminomethane buffer [100 millimolar, pH 7.5] in water (FIG. 1, Box 1). The reaction was allowed to incubate for 10 seconds, after which 200 microliters of a solution of 5% acetic acid in water was added (FIG. 1, Box 2). The acceptor product was separated from the adenosine triphosphate and adenosine diphosphate using a Microcon 3000 molecular weight cut off (MWCO) ultrafilter, available from Millipore Corporate Headquarters, 290 Concord Road, Billerica, Mass. 01821, USA (FIG. 1, Box 3). The NADP was measured using an x-ray fluorescence spectrometer equipped with a 50 watt chromium anode x-ray tube and a silicon drift detector (FIG. 1, Box 4). The ratio of the phosphorus x-ray fluorescence signal to sulfur x-ray fluorescence signal was 0.030501 for the NAD, and 0.264657 for the phosphorylated NAD.

Figure 3:
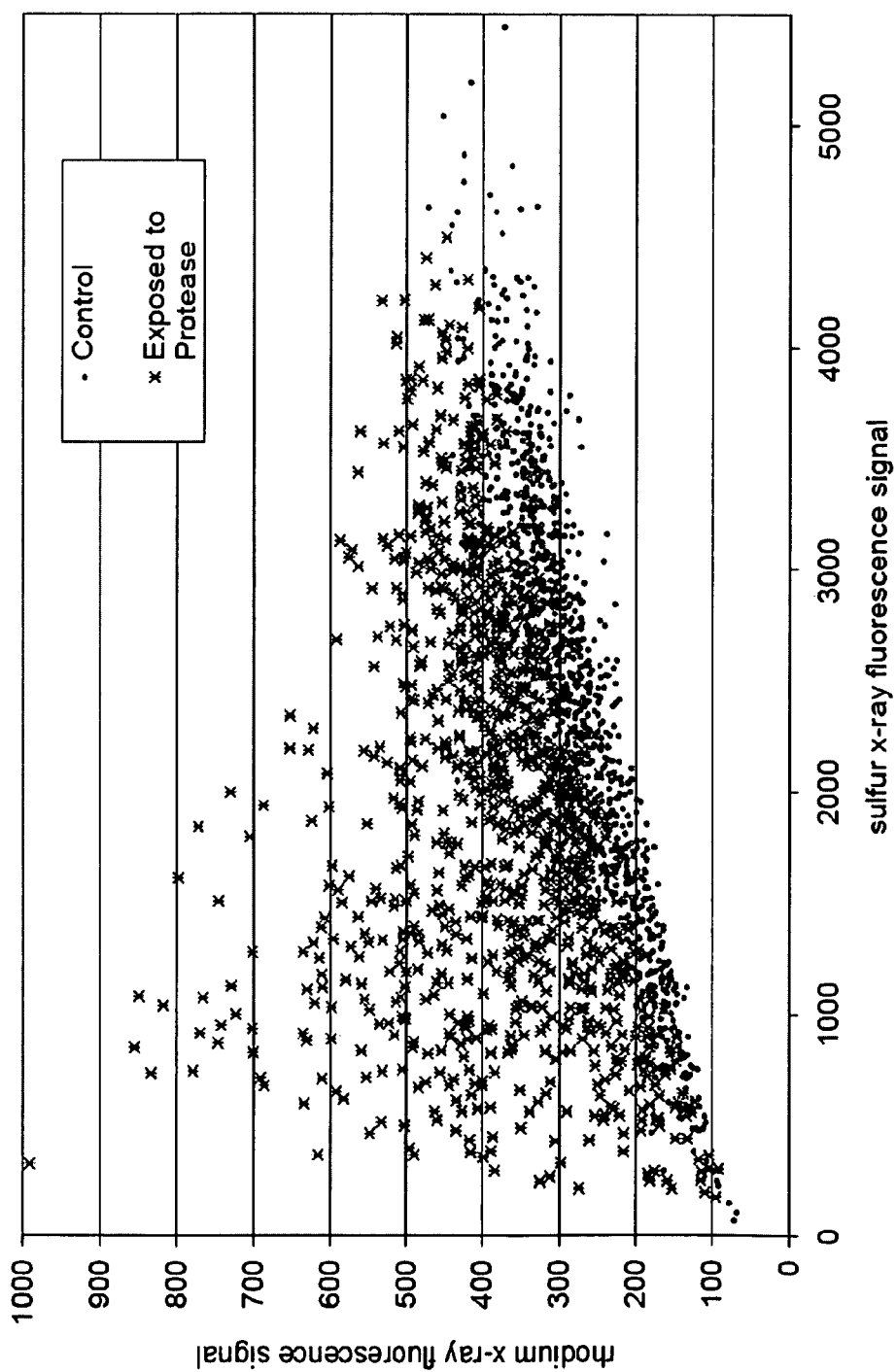
FIG. 3 shows data obtained by using the method of the present invention as described in Example 2.

Example 2. A set of peptides having the formula: polystyrene bead-LINKER-cysteine$_1$-xxx$_1$-xxx$_2$-xxx$_3$-xxx$_4$-cysteine$_2$, where xxx$_1$, xxx$_2$, xxx$_3$, and xxx$_4$ are independently selected from the amino acids {alanine, arginine, asparagine, aspartic acid, glutamine, glutamic acid, glycine, histidine, isoleucine, leucine, lysine, phenylalanine, proline, serine, threonine, tryptophan, tyrosine, and valine} served as the donor chemical. "Polystyrene bead-LINKER" refers to AM resin such as available from Rapp Polymere GmbH, Ernst-Simon-Str. 9, D 72072 Tubingen, Germany. Water served as the acceptor chemical. Trypsin and $K_2PtCl_4$ served as controller chemicals. The peptides having the formula: polystyrene bead-LINKER-cysteine$_1$-xxx$_1$-xxx$_2$-xxx$_3$-xxx$_4$-$CO_2H$ served as the donor product, where xxx$_1$, xxx$_2$, xxx$_3$, and xxx$_4$ are independently selected from the amino acids {alanine, arginine, asparagine, aspartic acid, glutamine, glutamic acid, glycine, histidine, isoleucine, leucine, lysine, phenylalanine, proline, serine, threonine, tryptophan, tyrosine, valine, and no amino acid} served as the donor chemical. The peptides having the formula: polystyrene bead: $H_2N$-xxx$_1$-xxx$_2$-xxx$_3$-xxx$_4$-cysteine served as the donor product, where xxx$_1$, xxx$_2$, xxx$_3$, and xxx$_4$ are independently selected from the amino acids {alanine, arginine, asparagine, aspartic acid, glutamine, glutamic acid, glycine, histidine, isoleucine, leucine, lysine, phenylalanine, proline, serine, threonine, tryptophan, tyrosine, valine, and no amino acid} served as the acceptor product. A 250 microliter solution was prepared of resin bound peptides [in suspension] and $K_2PtCl_4$ [50 mM]; this solution was incubated for 4 hours, after which 500 microliters of porcine trypsin [45 micromolar] and ammonium bicarbonate [40 millimolar] was added (FIG. 1, Box 1). The solution was incubated for 16 hours (FIG. 1, Box 2), after which the resin beads were filtered and rinsed twice with water to separate any unreacted donor chemical from the acceptor product (FIG. 1, Box 3). The donor products were measured using an x-ray fluorescence spectrometer equipped with a 60 watt rhodium anode x-ray tube and a silicon drift detector (FIG. 1, Box 4). The ratio of the sulfur x-ray fluorescence signal to the rhodium x-ray fluorescence signal was plotted, and FIG. 3 shows the plotted data. Control samples of donor chemical were described by the equation: (Rh)=0.0706(S)+106.03, where (Rh) is the rhodium x-ray fluorescence signal, (S) is the sulfur x-ray fluorescence signal. This data is labeled as "Control" in FIG. 3. Many of the donor chemical which had been subjected to the above reaction conditions had a higher ratio of rhodium x-ray fluorescence signals to sulfur x-ray fluorescence signal, indicating that the trypsin had removed cysteine$_2$ with varying efficiencies. This data is labeled as "Exposed to Protease" in FIG. 3. None of the donor chemical which had been subjected to the above reaction conditions had sulfur x-ray fluorescence signals of zero, indicating that the trypsin had not removed cysteine$_1$ from any bead completely.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for analyzing reactions, comprising:
   (a) providing a solution comprising solvent, at least one acceptor chemical and at least one donor chemical, wherein the donor chemical is capable of donating a chemical moiety comprising a chemical element to the acceptor chemical, and at least two controller chemicals capable of affecting the reaction between the donor chemical and the acceptor chemical;
   (b) incubating the solution to allow a portion of the acceptor chemical to react with the donor chemical to form an acceptor product;
   (c) separating at least a portion of the unreacted donor chemical from the acceptor product;
   (d) removing at least a portion of the solvent before measuring using x-ray fluorescence at least one of the chemicals selected from the list of acceptor product and the donor chemical; and (e) measuring using x-ray fluorescence at least one of the acceptor product or the donor chemical, wherein:
the controller chemicals are selected from the group consisting of amino acids, lipids, reactive oxygen species and reactive nitrogen species; and
the sample of donor chemical or acceptor product that is subjected to x-ray fluorescence measurement is concentrated such that the area containing more than 50% of the sample based on the total amount of the sample of donor chemical or acceptor product that is subjected to x-ray fluorescence measurement is less than 0.005 square centimeters.

2. The method of claim 1, further comprising:
measuring using at least one additional analytical method at least one of the acceptor product or the donor chemical.

3. The method of claim 1, wherein the step of removing at least a portion of the solvent is performed using reduced pressure.

4. The method of claim 1, wherein at least 80% of the solvent is removed.

5. The method of claim 4, wherein the step of separating at least a portion of the unreacted donor chemical from the acceptor product is performed using chromatography.

6. The method of claim 4, wherein the step of separating at least a portion of the unreacted donor chemical from the acceptor product is performed using a centrifuge.

7. The method of claim 4, wherein the step of separating at least a portion of the unreacted donor chemical from the acceptor product is performed using size exclusion chromatography.

8. The method of claim 1, wherein the reaction between the donor chemical and the acceptor chemical forms at least one chemical bond.

9. The method of claim 1, wherein the reaction between the donor chemical and the acceptor chemical breaks at least one bond.

10. The method of claim 1, wherein the controller chemical is an amino acid.

11. The method of claim 1, wherein the controller chemical is a reactive oxygen species.

12. The method of claim 1, wherein the controller chemical is a reactive nitrogen species.

13. The method of claim 1, wherein the controller chemical is a lipid.

* * * * *

UNITED STATES PATENT AND TRADEMARK OFFICE
CERTIFICATE OF CORRECTION

| | |
|---|---|
| PATENT NO. | : 10,577,642 B2 |
| APPLICATION NO. | : 15/961480 |
| DATED | : March 3, 2020 |
| INVENTOR(S) | : Eva R. Birnbaum |

Page 1 of 1

It is certified that error appears in the above-identified patent and that said Letters Patent is hereby corrected as shown below:

In the Specification

At Column 1, Line 15 (Approx.), add:
--STATEMENT REGARDING FEDERALLY SPONSORED R&D
This invention was made with government support under W81XWH-07-2-0017 awarded by the U.S. Army Medical Research & Development Command. The government has certain rights in the invention.--.

Signed and Sealed this
Sixteenth Day of April, 2024

Katherine Kelly Vidal
*Director of the United States Patent and Trademark Office*